United States Patent
Rosner

(10) Patent No.: US 6,597,758 B1
(45) Date of Patent: Jul. 22, 2003

(54) ELEMENTALLY SPECIFIC X-RAY IMAGING APPARATUS AND METHOD

(75) Inventor: S. Jeffrey Rosner, Palo Alto, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 10/140,617

(22) Filed: May 6, 2002

(51) Int. Cl.[7] .............................................. G01N 23/06
(52) U.S. Cl. ........................................ 378/53; 378/156
(58) Field of Search ............................ 378/53, 156–159

(56) References Cited
U.S. PATENT DOCUMENTS 4,910,757 A * 3/1990 Kiyasu et al. ................. 378/53

\* cited by examiner

*Primary Examiner*—Craig E. Church

(57) ABSTRACT

An apparatus for imaging features of an object constructed from a material that includes a first element in the presence of features constructed from a material that includes a second element. The apparatus utilizes a filtered x-ray spectrum to image the object. The filtered x-ray spectrum is generated from a polychromatic x-ray source having energies below a maximum energy. The maximum energy is greater than a dominant absorption edge of the first element. The filter includes a filter element having a dominant absorption edge greater than or equal to a dominant absorption edge of the second element. The filter removes x-rays that would otherwise be absorbed by the second element, thereby improving the relative contrast of images based on x-ray absorption of the first element.

15 Claims, 2 Drawing Sheets

ELEMENTALLY SPECIFIC X-RAY IMAGING APPARATUS AND METHOD

FIELD OF THE INVENTION

The present invention relates to x-ray imaging, and more particularly, to x-ray imaging techniques that can distinguish different elemental substances within the object being imaged.

BACKGROUND OF THE INVENTION

In x-ray transmission imaging, illumination is projected through an object and the imaging signal results from a subtractive process, i.e. what is imaged is the far field of the illuminations minus any signal that was absorbed, reflected or scattered. In many industries x-ray inspection is being used routinely for inspection of products in the manufacturing environments. Many of these applications require that a particular material be examined in the inspection process in spite of the presence of other materials that also absorb x-rays. For example, surface mounted integrated circuits are examined during manufacture to determine the distribution of solder on the assembly, which in turn, is related to the reliability of the assembly. In such systems, Cu traces, Si chips, and Fe in transformers all conspire to obscure, or 'shadow' the solder joints. Similar problems exist today in the use of x-ray imaging in the food processing industry for foreign object identification, the molding and casting industry for real-time mold-fill visualization, the transportation industry for contraband detection, etc. Hence, techniques that provide some specificity to distinguish between the various overlaid features are needed. In the following discussion, "specificity" is defined as the ability to enhance the contrast of one material with respect to the contrast of an interfering material.

One example where specificity has been accomplished is in the medical use of dual energy imaging to measure bone density and/or body fat. By exploiting the fact that bone absorbs x-rays to higher energies, two images are taken using different accelerating voltages in the x-ray tube. Simple algebra is used to combine these images in a manner that accentuates the less or more absorbing x-rays and provide a 'bone image' or a 'fat image'. However, this technique requires that two images with exact registration must be taken; hence, any motion of the object (patient) shows up as an inaccuracy. Since it takes several seconds to reset the tube energy, these registration artifacts are difficult to eliminate. In principle, two x-ray sources can be used to take the images, but this increases the system cost and requires periodic calibration to register the two sources.

In principle, the desired specificity can be provided by using a single energy source with a detector that has the ability to detect the energies of the x-rays that reach the detector. For example, U.S. Pat. No. 5,943,388 describes a discrete detector for use with a broad energy range polychromatic illumination source. In this approach, active pixels are created by discrete detectors coupled to a multichannel analyzer that detects each x-ray photon arriving at each pixel. The photons are counted in bins corresponding to a pre-defined set of energy windows. Each energy window corresponds to a different image. By correctly choosing energy windows that are specifically affected by particular materials, significant improvements in specificity can be achieved. Unfortunately, the cost of the detectors for such a scheme significantly increases the cost of the imaging systems.

All of the previously discussed approaches rely on either imaging using two separately produced spectra with differing energy distributions, which requires the complexity of multiple sources or the delays of energy varying in real-time or energy discrimination in the pixelated detector, with the attendant electronic complexity and cost.

Additionally, there are a number of rastering schemes (similar to the operation of a scanning electron microscope) for building up a material-specific image using a well-defined x-ray spot and a single detector in which the image is reproduced pixel by pixel. Unfortunately, the throughput of such schemes is severely limited by two factors. First, it is difficult to focus x-rays (particularly at industrially relevant energies). A small spot must generally be created by collimation, which substantially reduces the flux of x-rays available for imaging. While this problem can be remedied by using a synchrotron to generate a collimated beam of x-rays, such accelerators are too expensive for routine imaging on production lines and the like. This renders these schemes only useful for failure analysis and scientific studies, as opposed to real-time quality control testing. Second, even if sufficient flux is obtained, the object must be moved for each pixel, requiring milliseconds per pixel to move and settle. Hence, these schemes are impractical if large images are needed.

Broadly, it is the object of the present invention to provide an improved apparatus and method for generating x-ray images having improved elemental specificity.

It is a further object of the present invention to provide an imaging instrument and method that is better suited to production line screening and the like.

These and other objects of the present invention will become apparent to those skilled in the art from the following detailed description of the invention and the accompanying drawings.

SUMMARY OF THE INVENTION

The present invention is an apparatus for imaging features of an object constructed from a material that includes a first element in the presence of features constructed from a material that includes a second element. The apparatus utilizes a filtered x-ray spectrum to image the object with the aid of an x-ray detector. The filtered x-ray spectrum is generated from a polychromatic x-ray source having a maximum energy that is determined by the absorption spectrum of the first element. The filter includes a filter element having a dominant absorption edge greater than or equal to the dominant absorption edge of the second element and less than the maximum energy. The filter removes x-rays that would otherwise be absorbed by the second element thereby improving the direct interpretation of contrast of images based on x-ray absorption of the first element.

DETAILED DESCRIPTION OF THE INVENTION

Figure 1:
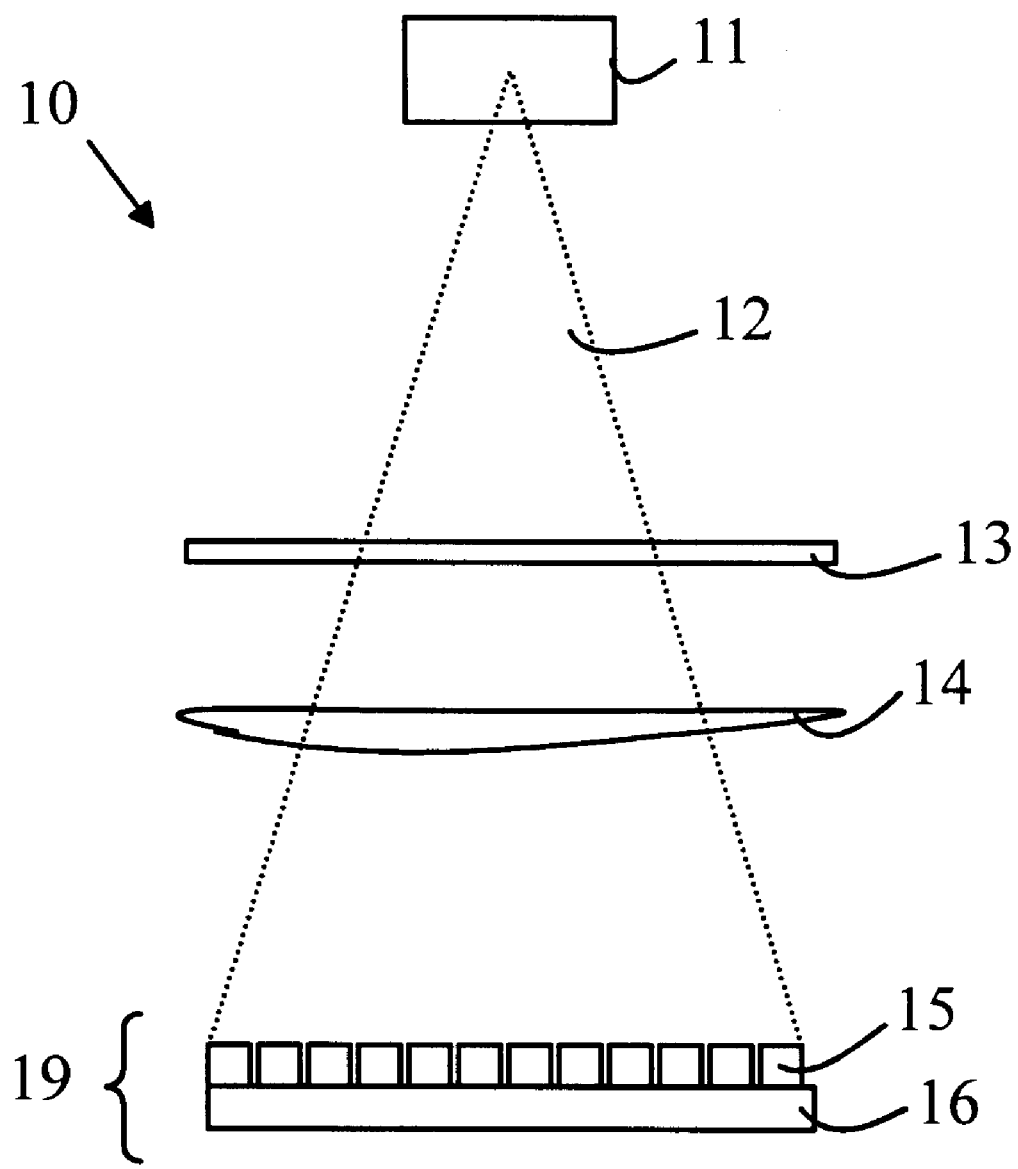
FIG. 1 is a cross-sectional view of an imaging system 10 according to the present invention operating on an object 14.

The manner in which the present invention provides its advantages can be more easily understood with reference to FIG. 1, which is a cross-sectional view of an imaging system 10 according to the present invention operating on an object 14. Imaging system 10 utilizes a conventional polychromatic x-ray energy source 11, which generates a useful cone of x-rays 12. The x-rays from source 11 are filtered by a filter 13 before impinging on the object 14. The manner in which this filter is constructed will be discussed in more detail below. The x-ray energy leaving the object at various points is detected by a pixelated, or 'imaging', x-ray detector 19. Such a detector, for example could include an x-ray detection material 15 that converts the x-rays incident thereon to visible light that is detected by a camera chip 16. Any imaging x-ray sensor, x-ray camera or the like can be used for this invention.

The manner in which this arrangement provides improved specificity can be more easily understood with reference to an imaging problem in which a heavy, or high atomic number, element, e.g., Pb, must be distinguished from a lighter, or lower atomic number, element, e.g. Cu. The present invention is based on the observation that for any given material and thickness combination, the images formed by an x-ray system depend on the energy spectrum generated by the x-ray source. In general, the x-ray spectrum provided by inexpensive x-ray sources is far from optimum for imaging features constructed from a high atomic number element in the presence of features constructed from a lower atomic number element. The present invention utilizes a filter to modify the spectrum of an x-ray source in a manner that enhances its ability to image specific elements in the presence of interfering elements.

There are two predominant features in elemental x-ray absorption in the industrially useful energy range of 0–250 keV. First, is the general decrease in absorption due to photoelectric absorption by valence electrons that is inversely proportional to the square of the x-ray energy. For any material and thickness, there is some energy where this absorption will dominate and create a sharp decrease in absorption. This energy will be referred to as a dominant absorption edge. Superimposed on this are sharp increases in the absorption at specific energies associated with photoelectric absorption by core shell electrons that create sharp increases in absorption followed by continuing decreases in absorption that is inversely proportional to the square of the x-ray energy. For example, Pb has a feature at the K-edge of about 87.9 keV, and Cu has a K-edge of about 8.98 keV. These features can be utilized to enhance image contrast. For example, a source spectrum with enhanced flux between the K-edge of Pb and an energy of about 140 keV will greatly improve Pb contrast in the presence of Cu in an image taken using this spectrum. In general, any dominant absorption edge or other significant absorbing feature in the absorption spectrum of the desired element in an energy range where the interfering element has reduced absorption may be utilized to improve the contrast of the desired element.

A conventional polychromatic x-ray source designed to maximize x-ray flux available for image formation is typically based on Brehmstrahlung radiation. Such sources have a characteristic broad energy distribution that may encompass many absorbing features and extend somewhat beyond the higher significant absorbing feature. The upper limit of the source spectrum is fixed by the choice of x-ray tube operating voltage so that some of the flux is absorbed by the core shell edge of the higher atomic number element to create contrast related to the distribution of that element in the object. Unfortunately, such a spectrum has a significant number of photons at lower energies, and hence, the low atomic number element absorbs a significant amount of the source energy and obscures the material from the higher atomic number element.

Consider one pixel in the final image. The intensity of the image at this pixel is proportional to the number of x-rays that pass through the object being imaged and reach the detector responsible for this pixel. Denote the total number of x-rays that pass through the pixel during an exposure with no object in place by N. When the object is in place, the number of x-rays reaching the detector is reduced by the x-rays that are absorbed by the Cu, denoted by $N_L$ and by the x-rays that are absorbed by the Pb, denoted by $N_H$. It is useful to define the contrast at the pixel as follows:

Contrast=1–[(integrated signal with object in place)/N]= $1-N_L/N-N_H/N$

This is essentially the contrast that would be observed by a detector that generates a signal that is independent of the energy of the incoming x-ray photons. It is clear that any element that absorbs x-rays from the source contributes to the contrast. In the case of Cu and Pb, the Cu selectively absorbs x-rays with energies just below the Cu dominant absorption edge. The Pb selectively absorbs x-rays with energies just above the Pb k-edge, which is the significant absorbing feature for Pb.

The present invention is based on the observation that the contrast caused by the Cu would be significantly reduced if the source did not include x-ray energies that are readily absorbed by the Cu. Hence, filter 13 discussed above is included in the imaging apparatus to absorb x-rays that would normally be absorbed by the Cu. The filter can be constructed from any material having a dominant absorption edge at or above that of the Cu and below the dominant absorption edge or other significant absorbing feature of the Pb.

In the preferred embodiment of the present invention, a material having a dominant absorption edge between that of the interfering material and that of the desired material is utilized. While Cu could be used for the filter in the case in which Cu is the interfering element, the dominant absorption edge of Cu is not absolutely sharp. Accordingly, some of the x-rays at energies around the Cu dominant absorption edge would leak through the filter. Hence, an element having a dominant absorption edge at a higher energy is utilized to assure that photons that would be absorbed by Cu are effectively removed. The choice of material depends on the ability to provide an effective economical filter. Bulk material cost, mechanical properties suitable for forming thin plate, low toxicity and reactivity, and corrosion resistance are factors in the choice of materials. For Cu imaging in the presence of Pb, a convenient choice is Mo, since other materials between Cu and Mo are more expensive and more difficult to handle.

One of the most economically viable imaging problems for electronics manufacturing involves enhancing Pb or Sn in a background of Cu, Si, or any other materials utilized in the integrated circuit fabrication, electronics packaging assembly and printed circuit manufacture. Such imaging provides the basis for finding faults in solder connections on the integrated circuits and/or circuit boards containing the same. In these cases, Mo is the preferred filter material for the reasons discussed above.

However, the present invention can also be utilized for enhancing the image of any structure constructed from a material partially or entirely composed of a first element, the "heavy" or high atomic number element, in the presence of a material partially or entirely composed of a second, "lighter" or lower atomic number element. In the general case, the filter is constructed from a material having a dominant absorption edge energy that is less than the energy of the absorbing feature of the absorption spectrum of the heavy element that is to be exploited and greater than or equal to the energy of the dominant absorption edge of the lighter interfering element.

Figure 2:
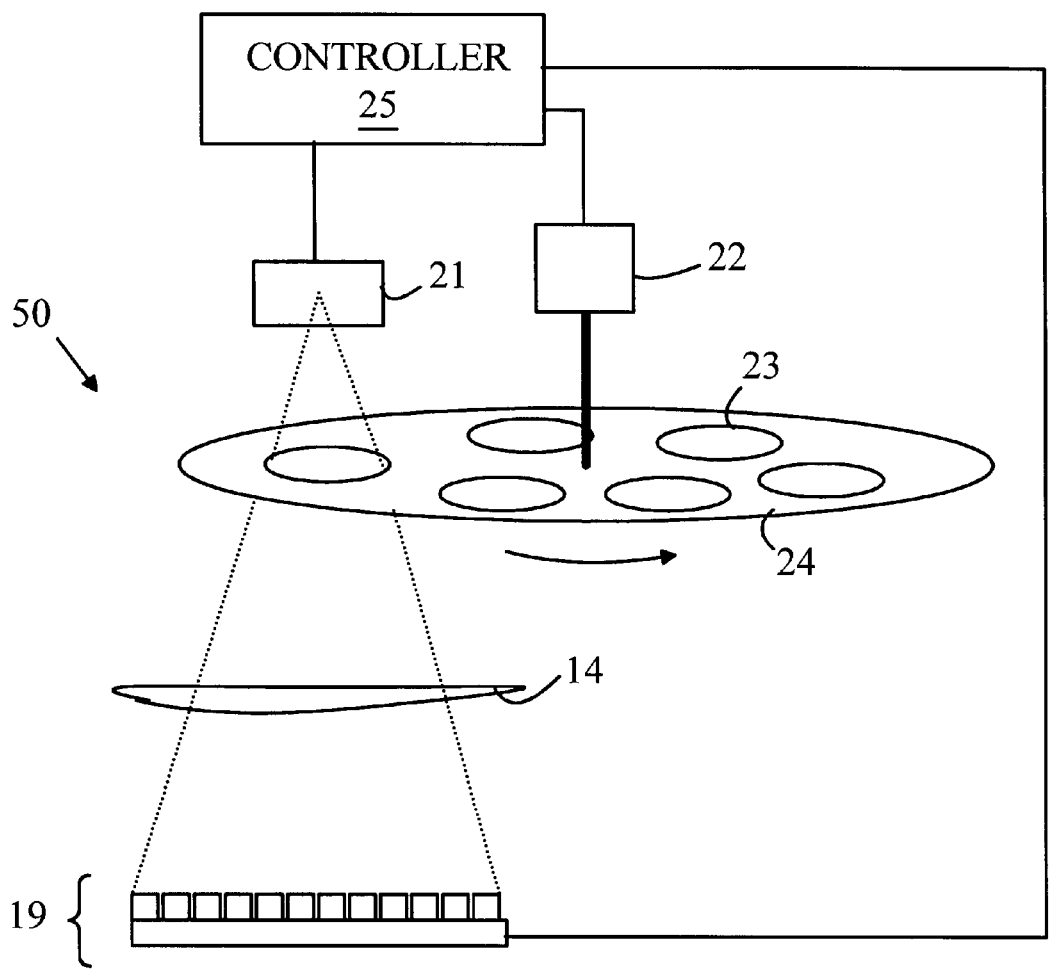
FIG. 2 illustrates another embodiment of an imaging system according to the present invention.

If a particular application requires the generation of images based on a number of different elements, multiple filters can be utilized. Refer now to FIG. 2, which is a schematic drawing of an imaging apparatus 50 according to the present invention. Apparatus 50 includes a mechanism 22 that rotates a wheel 24 having a plurality of filter elements 23. The filter elements are rotated into the beam from x-ray source 21. Image detector 19 forms an image of object 14 with each filter in place. For the highest throughput performance, the acceleration potential in the x-ray source would remain constant; this is the preferred embodiment for applications where this provides adequate specificity. In principle, the acceleration potential in x-ray source 21 can be adjusted for each filter element such that the x-ray spectrum leaving the filter element is peaked at some energy between the dominant absorption edge of the filter material and the high energy end of the spectrum from source 21. In this case, each image is selectively enhanced for elements having a significant absorbing feature within the energy range provided at the exit side of the filter.

It should be noted that while this scheme provides considerable enhancement for elements having a significant absorbing feature within this spectral range, interference from elements having significant absorbing features at higher energies can also be present. This interference can be removed by combining a number of different images, each taken with a different filter and energy spectrum. For example, if there are 5 elements of interest in object 14, weighted combinations of the corresponding pixels in each of 5 images can be used to determine the concentration of each element seen by that pixel, and hence, create images based on each element. The weight factors depend on the efficiency with which each element contributes to each image when a particular filter and energy spectrum is used.

It should be noted that preferred embodiments can be practiced in which the end point of the x-ray spectrum generated by source 21 is not altered for each filter. In applications in which image collection time is critical, the time required to change the acceleration voltage in source 21 and allow the source to settle can be prohibitively large. In industrial applications, throughput is very important, and hence, avoiding such delays is useful in such applications. In addition, the cost of providing a programmable high-voltage power supply can significantly increase the cost of the apparatus.

In embodiments where images with sufficient elemental specificity can be formed from weighted sums of the raw images taken with various filters, the endpoint need not be altered. In effect, the weighting coefficients used in the various linear combinations of the images can take this information into account. In addition, if a difference image is formed between two images taken with different filters, the image that would have resulted from the lower energy filter and a reduced energy x-ray source is obtained.

Practical candidates for filters are well-spaced through the periodic table, e.g. Be, C, Al, Si, all the $1^{st}$ row transition elements from Ti→Zn, Mo, Ag, Sn, Ta, W, Au, and Nb can all be utilized as filter elements. In addition to the filters discussed above, wheel 24 may include gaps to aid in the calibration of the x-ray source/detector combination and provide an unfiltered reference image.

The x-ray source must have sufficient intensity at energies around the significant absorbing feature of the desired element. Hence, the source is adjusted to provide a spectrum that extends above the significant absorbing feature of the desired element sufficiently to provide good imaging.

The optimum thickness for such a filter depends on a tradeoff between increasing contrast between the high and low atomic number elements while still leaving a sufficient number of x-ray photons capable of imaging the high atomic number elements. This is necessary because even a well-chosen material does in fact absorb somewhat above a dominant absorption edge of the high atomic number material. For Pb imaging with a Mo filter in the presence of Cu, filter thicknesses of 250–3000 $\mu$m have proven useful, with a likely optimum in the 500 $\mu$m or 20 mil range.

Various modifications to the present invention will become apparent to those skilled in the art from the foregoing description and accompanying drawings. Accordingly, the present invention is to be limited solely by the scope of the following claims.

What is claimed is:

1. An apparatus for imaging features of an object constructed from a material including a first element in the presence of features constructed from a material including a second element, said apparatus comprising:
   a polychromatic x-ray source for generating x-rays that have energies below a maximum energy, said maximum energy being determined by the absorption spectrum of said first element;
   a filter for selectively removing x-rays from said polychromatic x-ray source, said filter comprising a first filter element having a dominant absorption edge with an energy greater than or equal to the energy of a dominant absorption edge of said second element and less than said maximum energy; and
   a detector for forming a first image based on the absorption of said x-rays from said filtered x-ray source by said object.

2. The apparatus of claim 1 wherein said first element is Pb and said first filter element is Mo, Ta, W, Sn, Zn, Cu, or Nb.

3. The apparatus of claim 1 wherein said first element is Sn, and said first filter element is Mo, Zn, Cu, or Nb.

4. The apparatus of claim 1 wherein said filter comprises a second filter element and a mechanism for substituting said second filter element for said first filter element, said second filter element being different from said first filter element.

5. The apparatus of claim 4 further comprising a controller for combining said first image with a second image based on said x-ray source with said second filter element.

6. The apparatus of claim 4 wherein said first and second filter elements are chosen from the group consisting of Be, C, Al, Si, all the $1^{st}$ row transition elements from Ti→Zn, Mo, Ag, Sn, Ta, W, Au, and Nb.

7. The apparatus of claim 4 wherein said mechanism for substituting said second element also comprises a controller for altering said maximum energy.

8. A method for imaging features of an object constructed from a material comprising a first element in the presence of features constructed from a material comprising a second element, said method comprising the steps of:
   generating x-rays having energies below a maximum energy, said maximum energy being determined by the absorption spectrum of said first element;
   filtering said generated x-rays through a filter comprising a filter element having a dominant absorption edge with an energy greater than or equal to the energy of a dominant absorption edge of said second element; and
   forming a first image of said object based on the absorption of said filtered x-rays by said object.

9. The method of claim 1 wherein said first element is Pb and said filter element is Mo, Ta, W, Sn, Zn, Cu, or Nb.

10. The method of claim 1 wherein said first element is Sn, and said filter element is Mo, Zn, Cu, or Nb.

11. The method of claim 8 wherein said first element is Sn, and said first filter element is Mo, Zn, Cu, or Nb.

12. The method of claim 8 wherein said step of filtering further comprises filtering said generated x-rays through a second filter element and forming a second image of said object based on the absorption of said x-rays from said filtered x-rays.

13. The method of claim 12 further comprising the step of combining said first and second images to form a third image.

14. The method of claim 11 wherein said first and second filter elements are chosen from the group consisting of Be, C, Al, Si, all the $1^{st}$ row transition elements from Ti→Zn, Mo, Ag, Sn, Ta, W, Au, and Nb.

15. The method of claim 11 further comprising changing said maximum energy when said x-rays are filtered through said second filter element.

* * * * *